(12) United States Patent
Turner et al.

(10) Patent No.: US 8,105,405 B2
(45) Date of Patent: Jan. 31, 2012

(54) QUICK RELEASE FILTER ASSEMBLY FOR PNEUMATIC SURGICAL MACHINE

(75) Inventors: Denis Turner, Vista, CA (US); Robert Palino, Alis Viejo, CA (US)

(73) Assignee: Novartis AG, Basel (CH)

( * ) Notice: Subject to any disclaimer, the term of this patent is extended or adjusted under 35 U.S.C. 154(b) by 1437 days.

(21) Appl. No.: 11/557,169

(22) Filed: Nov. 7, 2006

(65) Prior Publication Data

US 2008/0108980 A1    May 8, 2008

(51) Int. Cl.
*B01D 50/00* (2006.01)
(52) U.S. Cl. .............................. 55/385.1; 55/DIG. 17
(58) Field of Classification Search .......... 55/385.1, 55/DIG. 17
See application file for complete search history.

(56) References Cited

U.S. PATENT DOCUMENTS

| 2,511,800 | A | 6/1950 | Wilkinson |
| 2,551,800 | A | 5/1951 | Hopkes |
| 4,670,006 | A | 6/1987 | Sinnett et al. |
| 5,176,628 | A | 1/1993 | Charles et al. |
| 6,645,277 | B1 * | 11/2003 | Franz et al. ............. 96/417 |

FOREIGN PATENT DOCUMENTS

| EP | 0 239 346 A2 | 9/1987 |
| EP | 0 239 346 A3 | 9/1987 |
| GB | 1236396 A | 6/1971 |
| WO | WO 2008/140540 A2 | 11/2008 |
| WO | WO 2008/140540 A3 | 11/2008 |

OTHER PUBLICATIONS

International Searching Authority, International Preliminary Report on Patentability, PCT/US2007/080517, May 12, 2009, 8 pages.
International Searching Authority, Written Opinion of the International Searching Authority, Internation Application No. PCT/US2007/080517, Mar. 24, 2009, 7 pages.

* cited by examiner

*Primary Examiner* — Robert A Hopkins

(57) ABSTRACT

A quick release filter assembly for a pneumatic module of a surgical machine includes a housing, an input port, an output port, a filter, and a flange. The housing has first and second sides, a top, and a bottom. The input port is located on the first side of the housing and is configured to permit gas to enter the housing. The output port is located on the second side of the housing and is configured to permit gas to exit the housing. The filter is located in the housing between the input port and the output port. The flange is rigidly connected to the housing along a periphery of the top of the housing. The flange extends outward along a plane generally parallel with the top of the housing. The flange has a mechanism for connecting the housing to a mounting portion of the pneumatic module. When the mechanism is disengaged, the filter assembly can be removed from the pneumatic module.

13 Claims, 6 Drawing Sheets

QUICK RELEASE FILTER ASSEMBLY FOR PNEUMATIC SURGICAL MACHINE

FIELD OF THE INVENTION

The present invention relates to a pneumatic module for a surgical machine and more particularly to a quick release filter assembly for such a module.

BACKGROUND OF THE INVENTION

Several conditions of the eye threaten sight. Epiretinal membrane (ERM), also known as macular pucker and cellophane retinopathy, is a condition characterized by growth of a membrane across the macula, or central retina of the eye. This condition may be thought of as the growth of scar tissue across the macula, thus interfering with central vision. The ERM typically contracts, causing distortion of the central retina, thus producing distortion of vision. Most patients will note that either straight objects appear wavy and crooked and/or central vision is reduced, depending on the severity of the condition.

Epiretinal membranes may be associated with other conditions of the eye, however, the large majority are idiopathic, which means that the cause is unknown. Some of the disorders which are occasionally associated with ERM's include previous retinal detachments and surgery thereof, inflammatory conditions (uveitis), retinal tears, and branch retinal vein occlusion (BRVO) and central retinal vein occlusion (CRVO).

Another condition is a macular hole. A macular hole is almost always a spontaneous development that occurs predominantly in aging women. The development of a macular hole progresses through several stages, and with each progressive stage the vision may worsen. It has been postulated that shrinkage of the vitreous humor may produce traction on the fovea (central macula), thereby producing the hole itself. However, the cause of macular holes remains under investigation.

The retina, which lines the inside of the posterior wall of the eye, may occasionally become detached for various reasons. Most commonly, retinal detachment occurs as a result of a tear or hole in the retina, which develops as a result of a posterior vitreous separation (PVS). The retinal tear or hole allows fluid to enter the subretinal space, thus detaching the retina.

The retina receives oxygen and nutrients from the underlying choroid (vascular layer) of the eye. When a retinal detachment occurs, the detached retina begins to dysfunction, and ultimately, necrosis (death) ensues as a result if the retina is not reattached to the underlying choroid. As such, a retinal detachment is an urgent condition. The detached retina should be recognized and treated promptly.

Vitreo-retinal procedures may be appropriate to treat these and other serious conditions of the back of the eye. Vitreo-retinal procedures include a variety of surgical and laser procedures performed to restore, preserve, and enhance vision. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

The vitreous is a normally clear, gel-like substance that fills the center of the eye. It makes up approximately ⅔ of the eye's volume, giving it form and shape before birth. Certain problems affecting the back of the eye may require a vitrectomy, or surgical removal of the vitreous. After a vitrectomy, the vitreous is replaced as the eye secretes aqueous and nutritive fluids.

A vitrectomy may be performed to clear blood and debris from the eye, to remove scar tissue, or to alleviate traction on the retina. Blood, inflammatory cells, debris, and scar tissue obscure light as it passes through the eye to the retina, resulting in blurred vision. The vitreous is also removed if it is pulling or tugging the retina from its normal position. Some of the most common eye conditions that require vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

The retinal surgeon performs the procedure through a microscope and special lenses designed to provide a clear image of the back of the eye. Several tiny incisions just a few millimeters in length are made on the sclera. The retinal surgeon inserts microsurgical instruments through the incisions such as a fiber optic light source to illuminate inside the eye, an infusion line to maintain the eye's shape during surgery, and instruments to cut and remove the vitreous.

A vitrectomy is often performed in conjunction with other procedures such as retinal detachment repair, macular hole surgery, and macular membrane peel. The length of the surgery depends on whether additional procedures are required and the overall health of the eye.

In a vitrectomy, the surgeon creates three tiny incisions in the eye for three separate instruments. These incisions are placed in the pars plana of the eye, which is located just behind the iris but in front of the retina. The instruments which pass through these incisions include a light pipe, an infusion port, and the vitrectomy cutting device. The light pipe is the equivalent of a microscopic high-intensity flashlight for use within the eye. The infusion port is required to replace fluid in the eye and maintain proper pressure within the eye. The vitrector, or cutting device, works like a tiny guillotine, with an oscillating microscopic cutter to remove the vitreous gel in a slow and controlled fashion. This prevents significant traction on the retina during the removal of the vitreous humor The surgical machines used to perform a vitrectomy and other surgeries on the posterior of the eye are very complex. Typically, such an ophthalmic surgical machine includes a main console to which numerous different tools are attached. The main console provides power to and controls the operation of the attached tools.

The attached tools typically include probes, scissors, forceps, illuminators, and infusion lines. Each of these tools is typically attached to the main surgical console. A computer in the main surgical console monitors and controls the operation of these tools. These tools also get their power from the main surgical console. Some of these tools are electrically powered while others are pneumatically powered.

In order to provide pneumatic power to the various tools, the main surgical console has a pneumatic or air distribution module. This pneumatic module conditions and supplies compressed air or gas to power the tools. Typically, the pneumatic module contains a filter and water separator to condition the compressed gas as it enters the surgical machine. The pneumatic module is connected to a cylinder that contains compressed gas. The compressed gas is delivered via tubing or a manifold to a filter where it is conditioned. The compressed gas exiting the filter is then fed to the remainder of the surgical machine to provide pneumatic power to tools.

The proper gas pressure must be provided by the pneumatic module to the tools in order to insure their proper operation. Providing too low or too high a gas pressure can lead to safety problems. Too low a gas pressure can lead to underperformance or non-performance of the operation of a tool. Providing too high a pressure can damage equipment or lead to a malfunction during surgery. In either case, the safety of the patient is compromised. The condition of the filter and water separator can adversely impact the operation of the machine. If the filter is worn or dirty, it needs to be replaced. Traditionally, replacing the filter has consumed a great deal of technician time, sometimes leading to the machine being out of service for extended periods of time. Since such ophthalmic surgical machines are used to preserve and restore sight, it is important to have them in working order quickly after a filter malfunction. It would be desirable to have a surgical machine with an quickly and easily replaceable filter.

SUMMARY OF THE INVENTION

In one embodiment consistent with the principles of the present invention, the present invention is a quick release filter assembly for a pneumatic module of a surgical machine. The quick release filter assembly includes a housing, an input port, an output port, a filter, and a flange. The housing has first and second sides, a top, and a bottom. The input port is located on the first side of the housing and is configured to permit gas to enter the housing. The output port is located on the second side of the housing and is configured to permit gas to exit the housing. The filter is located in the housing between the input port and the output port. The flange is rigidly connected to the housing along a periphery of the top of the housing. The flange extends outward along a plane generally parallel with the top of the housing. The flange has a mechanism for connecting the housing to a mounting portion of the pneumatic module. When the mechanism is disengaged, the filter assembly can be removed from the pneumatic module.

In another embodiment consistent with the principles of the present invention, the present invention is quick release filter assembly for a pneumatic module of an ophthalmic surgical machine. The quick release filter assembly includes a generally cylindrical housing, an input port, an output port, a filter, and a flange. The generally cylindrical housing has an outer surface, a top surface, and a bottom surface. The input port is located on the outer surface of the housing and is configured to permit gas to enter the housing. The output port is located on the outer surface of the housing opposite the input port and is configured to permit gas to exit the housing. The filter is located in the housing between the input port and the output port such that gas entering the housing through the input port is filtered before exiting the housing through the output port. The flange is rigidly connected to the housing along a periphery of the top of the housing. The flange extends outward along a plane generally parallel to the top surface of the housing. The flange has a generally concave bottom surface adapted to fit with a ridge located on the pneumatic module. The flange has two holes extending from a top surface of the flange to the bottom surface of the flange. The two holes are adapted to accept two screws. When the two screws are removed from the two holes, the filter assembly can be removed from the pneumatic module.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
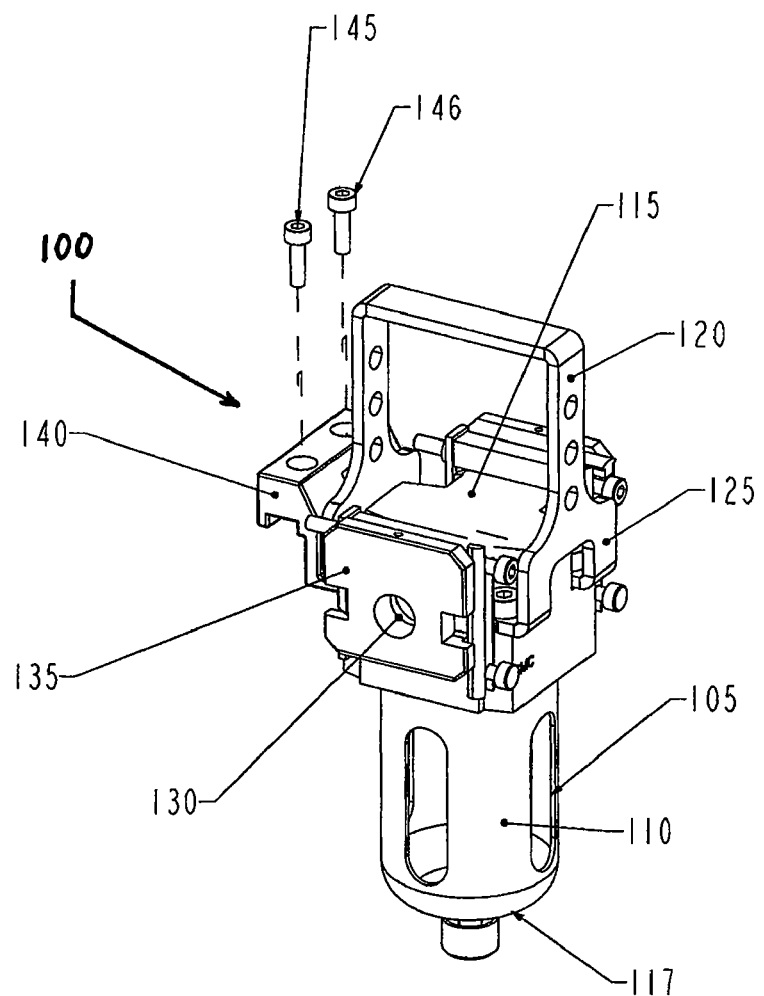
FIG. 1 is a perspective view of a quick release filter assembly according to an embodiment of the present invention.

FIG. 1 is a perspective view of a quick release filter assembly according to an embodiment of the present invention. In FIG. 1, the quick release filter assembly includes housing 105, input port 130, input port face plate 135, flange 140, and handle 120. Handle 120 is connected to housing 105 via handle connection 125.

Housing 105 extends from bottom surface 117 to top surface 115. Housing 105 also has an outer surface 110. In the embodiment of FIG. 1, housing 105 is generally cylindrical in shape. While being depicted as being generally cylindrical in shape, housing 105 may be any shape designed to fit with a pneumatic module. Housing 105 contains a filter (not shown) and a water separator (not shown). Housing 105 may be constructed of any convenient material, such as aluminum.

Input port face plate 135 is affixed to housing outer surface 110. Input port 130 is located on housing outer surface 110. Input port 130 extends from an outer surface of input port face plate 135 and through housing 105. In this manner, input port 130 allows gas to enter housing 105. Input port face plate 135 is configured to fit with a manifold of the pneumatic module (not shown) and form an air-tight seal. In this manner, gas located in a manifold of the pneumatic module (not shown) can enter housing 105 through input port 130. An output port (not shown) is located on housing outer surface 110 generally opposite input port 130.

Handle 120 is attached to housing 105 via handle connection 125. Handle 120 is located above the top surface 115 of housing 105. In one embodiment consistent with the principles of the present invention, handle 120 is pivotable about an axis that lies in a plane generally parallel with top surface 115 of housing 105. In this manner, handle 120 may be pivoted in a direction toward input port 130. In this case, handle 120 may be in a resting position on top surface 115 of housing 105. In another embodiment consistent with the principles of the present invention, handle 120 may be removable from housing 105. In this manner, handle 120 may snap onto housing 105 when it is necessary to remove filter assembly 100. In other embodiments of the present invention, handle 120 may be absent altogether.

Flange 140 is located on a periphery of the top surface 115 of housing 105. Flange 140 extends outward from top surface 115 of housing 105. In this manner, flange 140 protrudes outward from housing 105. While depicted as being adjacent to top surface 115 of housing 105, flange 140 may also be located between top surface 115 and bottom surface 117 of housing 105. In this manner, flange 140 can be located on housing 105. Regardless of the location, flange 140 is rigidly attached to housing 105 so that it can serve to secure housing 105 to the pneumatic module (not shown).

Flange 140 has a generally rectilinear or cuboid shape. As described in more detail in FIG. 4, flange 140 is adapted to secure filter assembly 100 to the pneumatic module. In the embodiment of FIG. 1, flange 140 has two holes adapted to receive two screws 145, 146. While the mechanism for securing filter assembly 100 to the pneumatic module (not shown) is a pair of screws 145, 146, other means can be used to secure filter assembly 100 to the pneumatic module (not shown). For example, a spring release device may be employed as may removable rivets. A snap on connector may also be used to secure filter assembly 100 to the pneumatic module.

In operation, gas enters housing 105 through input port 130 and exits housing 105 through an output port (not shown) generally opposite the input port 130. The gas that enters housing 105 passes through a filter (not shown) before exiting through the output port (not shown). In this manner, the gas is conditioned by the filter.

Removing the filter assembly 100 is an easy process. In the embodiment of FIG. 1, after two screws 145, 146 are removed, filter assembly 100 can be taken out of the pneumatic module. In other embodiments, the mechanism that holds filter assembly 100 to the pneumatic housing is disengaged thus allowing the filter assembly to be removed.

Figure 2:
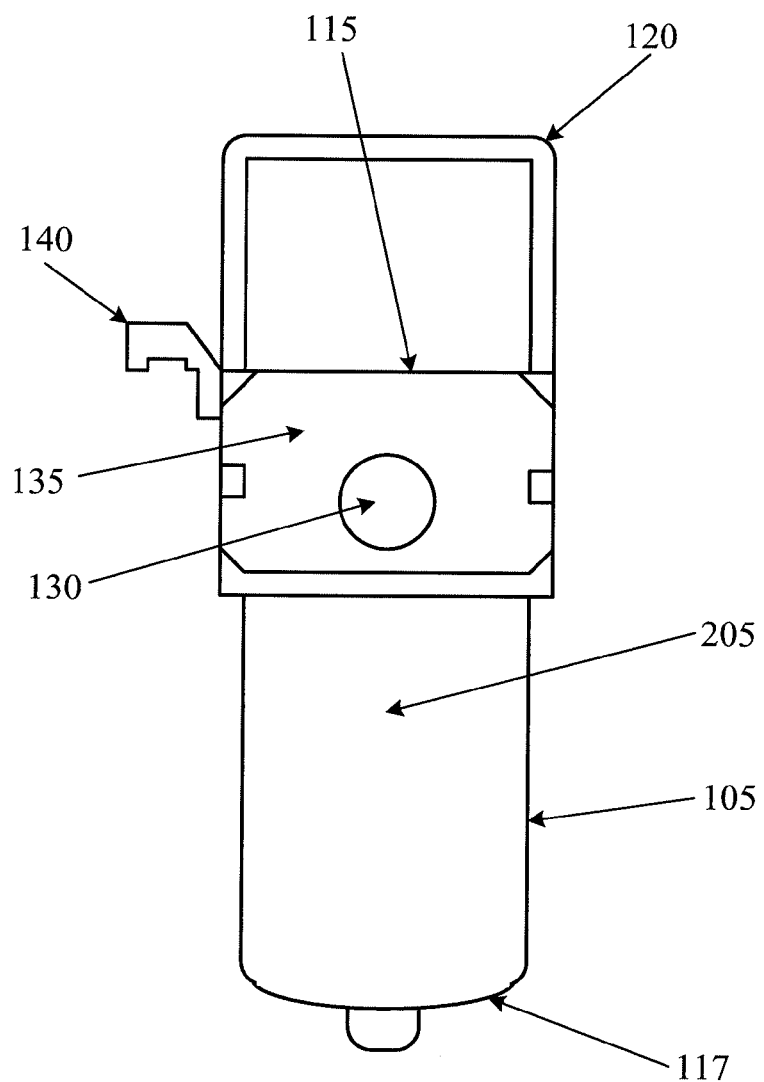
FIG. 2 is a front view of a quick release filter assembly according to an embodiment of the present invention.

FIG. 2 is a front view of the filter assembly 100 of FIG. 1. In FIG. 2, the components of the filter assembly that are visible include housing 105, handle 120, input port 130, input port face plate 135, and flange 140. As shown, input port face plate 135 and input port 130 are located on a first side 205 of housing 105. An output port (not shown) is located on a second side of housing 105 generally opposite input port 130.

As previously described, flange 140 is rigidly connected to housing 105 along a periphery of the top surface 115 of housing 105. Flange 140 has a generally concave bottom surface adapted to fit with the pneumatic module. In the embodiment depicted in FIG. 2, handle 120 may be rotated toward and away from the reader.

Figure 3:
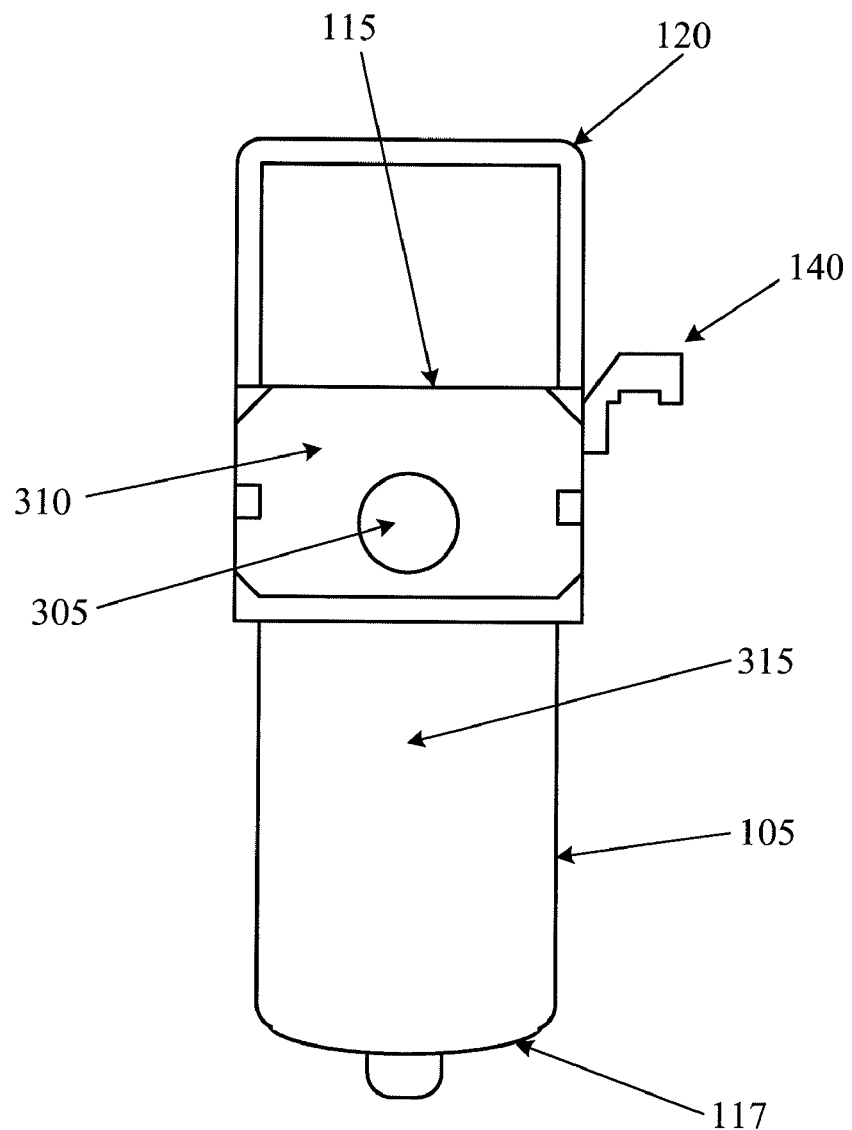
FIG. 3 is a back view of a quick release filter assembly according to an embodiment of the present invention.

FIG. 3 is a back view of the filter assembly 100 of FIG. 1. In FIG. 3, the components of the filter assembly that are visible include housing 105, handle 120, output port 305, output port face plate 310, and flange 140. As shown, output port face plate 310 and output port 305 are located on a second side 315 of housing 105. The input port (not shown) is located on a first side of housing 105 generally opposite output port 305.

As previously described, flange 140 is rigidly connected to housing 105 along a periphery of the top surface 115 of housing 105. Flange 140 has a generally concave bottom surface adapted to fit with the pneumatic module. In the embodiment depicted in FIG. 3, handle 120 may be rotated toward and away from the reader.

Figure 4:
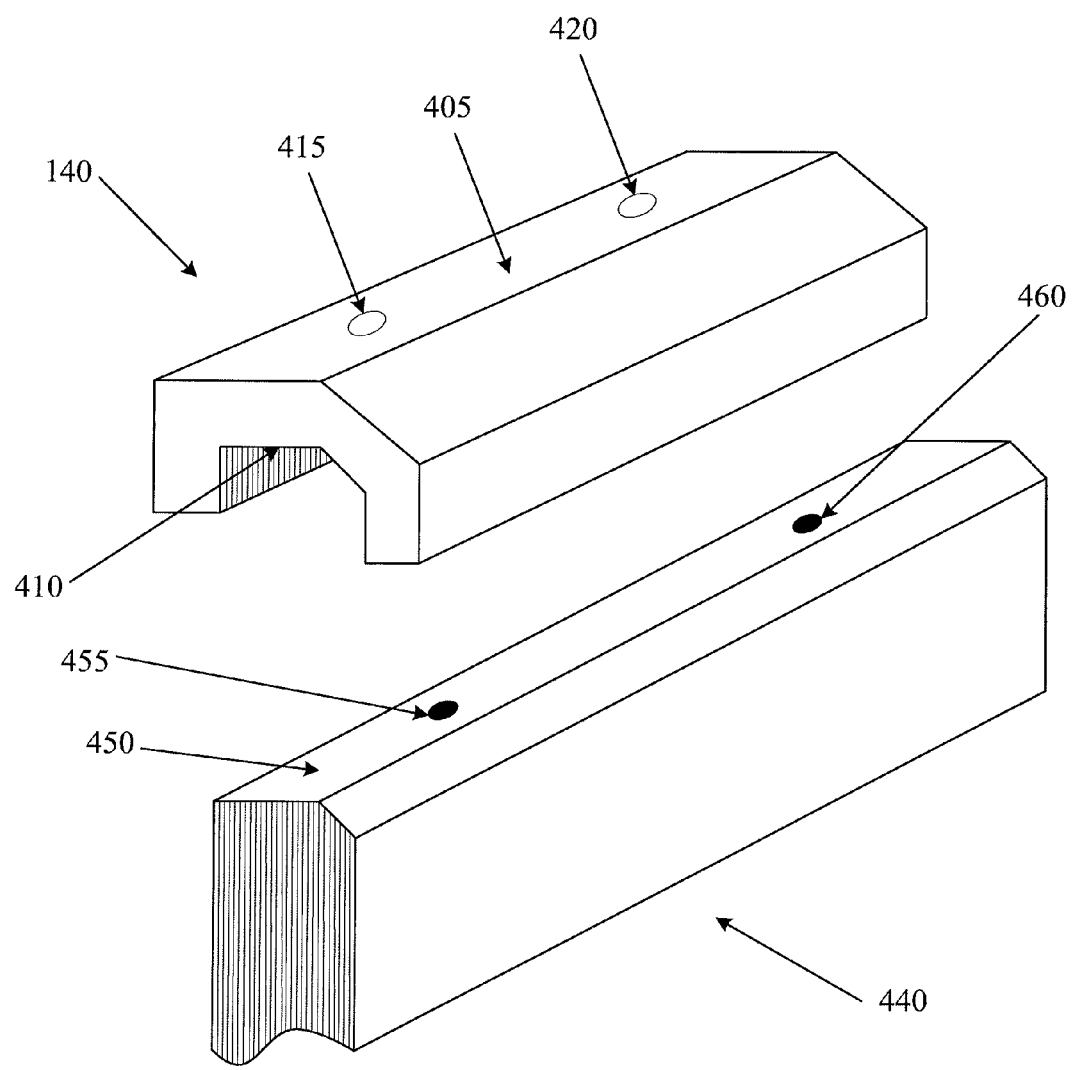
FIG. 4 is a detailed view of a flange used to connect the filter assembly to the pneumatic module according to an embodiment of the present invention.

FIG. 4 is a perspective view of one embodiment of the flange 140 of FIGS. 1-3 according to the principles of the present invention. In FIG. 4, flange 140 has a top surface 405 and a bottom surface 410. Two holes 415, 420 extend from the top surface 405 of flange 140 to the bottom surface 410 of flange 140. These two holes 415, 420 are each adapted to receive a screw for fastening the flange 140 to mounting portion 440 of the pneumatic module. Mounting portion 440 of the pneumatic module has a top surface 450. Two threaded holes 455, 460 extend downward from the top surface 450 of the pneumatic module. The two threaded holes 455, 460 are each adapted to receive a screw.

As shown in the embodiment of FIG. 4, flange 140 is a generally U-shaped rectilinear body. Bottom surface 410 of flange 140 is generally concave in shape. The shape of bottom surface 410 of flange 140 is adapted to fit over top surface 450 of mounting portion 440 of the pneumatic module. In this manner, flange 140 is adapted to connect with mounting portion 440 of the pneumatic console. When connected together, bottom surface 410 of flange 140 rests on top surface 450 of mounting portion 440.

Two screws (not shown) can be inserted into two holes 415, 420 on top surface 405 of flange 140. When flange 140 is on top of mounting portion 440, the screws can then be threaded into the two threaded holes 455, 460 on the top surface 450 of mounting portion 440. In this manner, flange 140 can be secured to mounting portion 440 of the pneumatic console with these two screws.

Figure 5:
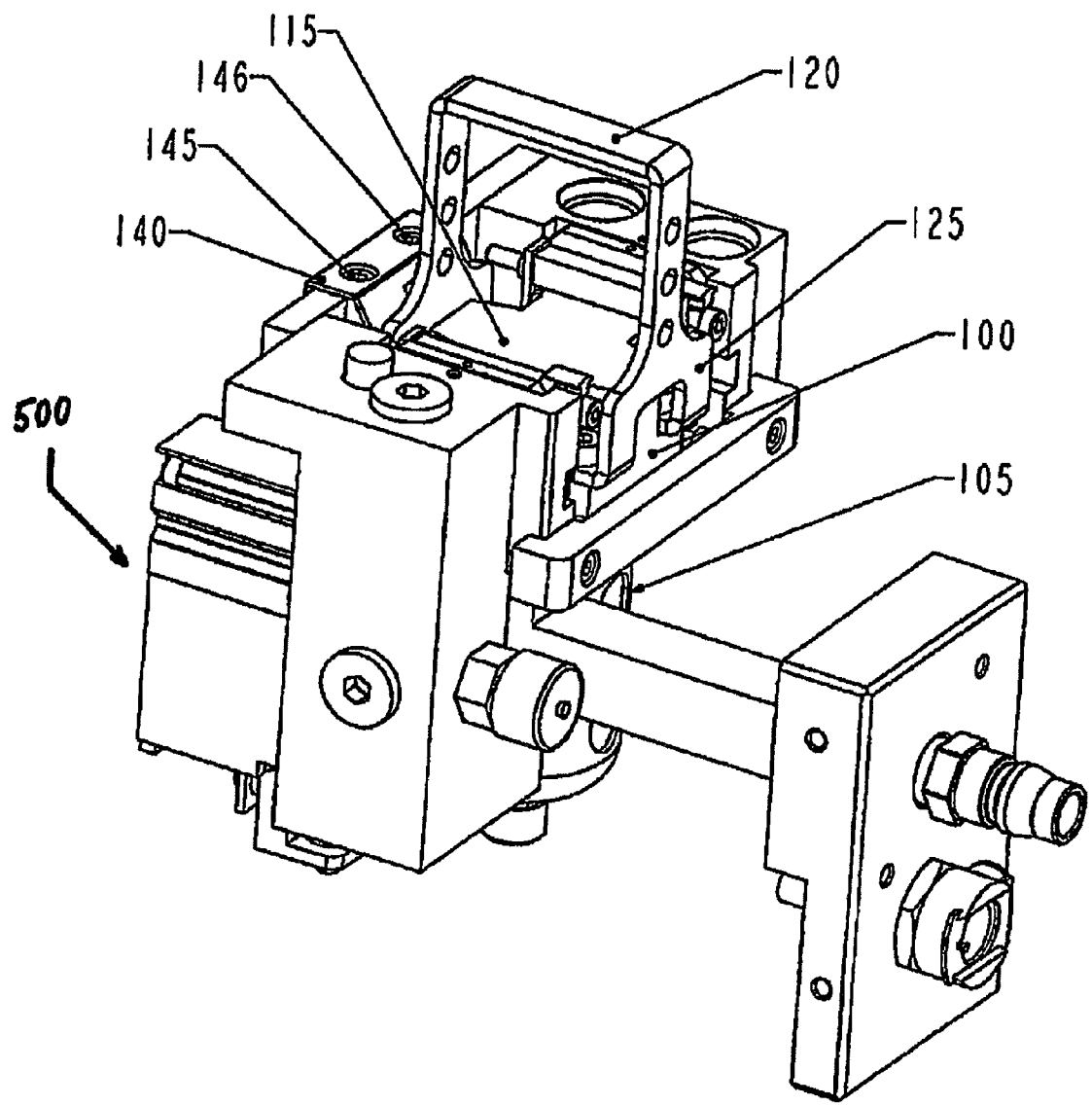
FIG. 5 is a perspective view of a pneumatic module with a quick release filter assembly according to an embodiment of the present invention.

FIG. 5 is a perspective view of a pneumatic module with a quick release filter assembly according to an embodiment of the present invention. In FIG. 5, filter assembly 100 is attached to pneumatic console 500. Filter assembly 100 includes housing 105, input port 130, input port face plate 135, flange 140, and handle 120. Handle 120 is connected to housing 105 via handle connection 125.

Pneumatic module 500 includes various manifolds, valves, and ports designed to direct the flow of compressed gas from a compressed gas source (not shown) to various pneumatically-powered tools (not shown). Pneumatic module 500 also has a mounting portion, which is located under flange 140 in the embodiment depicted in FIG. 5.

In FIG. 5, filter assembly 100 is connected to pneumatic module 500 with two screws 145, 146. These two screws 145, 146 attach flange 140 to mounting portion (located under flange 140) on pneumatic module 500. In this position, filter assembly 100 is secured to pneumatic module 500. The input and output ports of filter assembly 100 are aligned with manifolds in pneumatic module 500. In this manner, gas entering pneumatic module 500 from a compressed gas source can pass through a manifold in pneumatic module 500, into the input port of the filter assembly 100, through the filter of the filter assembly 100, out of the output port of the filter assembly 100, and into another manifold of pneumatic module 500.

Figure 6:
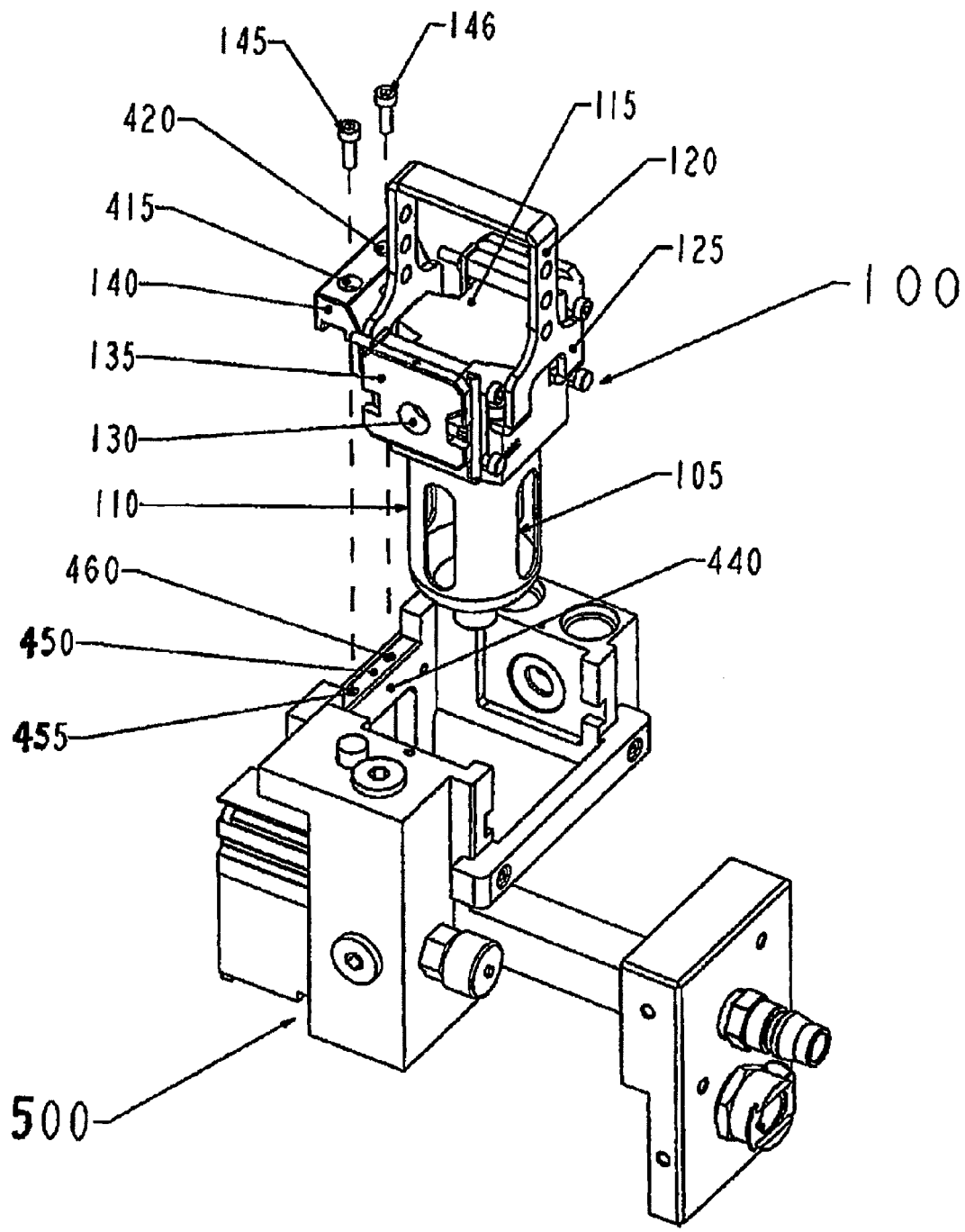
FIG. 6 is a perspective view of a pneumatic module with a quick release filter assembly according to an embodiment of the present invention.

FIG. 6 is a perspective view of a pneumatic module with a quick release filter assembly according to an embodiment of the present invention. In FIG. 6, filter assembly 100 has been removed from pneumatic module 500. As in previous drawings, filter assembly 100 includes housing 105, input port 130, input port face plate 135, flange 140, and handle 120. Handle 120 is connected to housing 105 via handle connection 125. Housing 105 has an outer surface 110. Flange 140 has two holes 415, 420, each adapted to receive one of two screws 145, 146.

Pneumatic module 500 includes various manifolds, valves, and ports designed to direct the flow of compressed gas from a compressed gas source (not shown) to various pneumatically-powered tools (not shown). Pneumatic module 500 also has a mounting portion 440 which is designed to connect to flange 140. Mounting portion 440 of pneumatic module 500 has a top surface 450 and two threaded holes 455, 460. The two threaded holes 455, 460 are each adapted to receive on of two screws 145, 146.

Filter assembly 100 is attached to pneumatic module 500 by moving it downward such that flange 140 interfaces with mounting portion 440. When the bottom surface of flange 140 contacts the top surface 450 of mounting portion 440, the two screws 145, 146 can be inserted into the two holes 415, 420 in flange 140 and threaded into the two threaded holes 455, 460 in mounting portion 440. In this manner, filter assembly 140 can be affixed to pneumatic module 440.

From the above, it may be appreciated that the present invention provides an improved filter assembly designed to be easy to service and replace. The present invention provides quick release filter assembly that can be easily removed and replaced so that the surgical machine can be put into service quickly. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A quick release filter assembly for a pneumatic module of a surgical machine comprising:
    a housing having first and second sides, a top, and a bottom;
    an input port located on the first side of the housing, the input port configured to permit gas to enter the housing;
    an output port located on the second side of the housing, the output port configured to permit gas to exit the housing;
    a filter located in the housing between the input port and the output port; and
    a flange rigidly connected to the housing, located along a periphery of the top of the housing, and extending outward along a plane generally parallel with the top of the housing, the flange having a mechanism for connecting the housing to a mounting portion of the pneumatic module;
    wherein when the mechanism is disengaged, the filter assembly can be removed from the pneumatic module.

2. The assembly of claim 1 wherein the filter further comprises a moisture separator.

3. The assembly of claim 1 further comprising:
    a handle located on the top of the housing, the handle adapted to be grasped by a hand.

4. The assembly of claim 3 wherein the handle is pivotable about an axis contained in a plane generally parallel to the top of the housing.

5. The assembly of claim 3 wherein the handle is adapted to be removed from the top face of the housing.

6. The assembly of claim 1 wherein the mechanism for connecting the housing to the mounting portion of the pneumatic module comprises two holes located on a top face of the flange and extending to a bottom face of the flange, the two holes adapted to receive two screws, the two screws adapted to threadably engage with the mounting portion of the pneumatic module.

7. The assembly of claim 1 wherein the housing is generally cylindrical in shape.

8. The assembly of claim 1 wherein gas entering the input port is filtered before exiting the output port.

9. The assembly of claim 1 wherein the flange has a generally concave bottom surface adapted to fit with the mounting portion of the pneumatic module, and further wherein the mounting portion of the pneumatic module is in the shape of a ridge.

10. A quick release filter assembly for a pneumatic module of an ophthalmic surgical machine comprising:
    a generally cylindrical housing having an outer surface, a top surface, and a bottom surface;
    an input port located on the outer surface of the housing, the input port configured to permit gas to enter the housing;
    an output port located on the outer surface of the housing opposite the input port, the output port configured to permit gas to exit the housing;
    a filter located in the housing between the input port and the output port such that gas entering the housing through the input port is filtered before exiting the housing through the output port;
    a flange rigidly connected to the housing along a periphery of the top of the housing, the flange extending outward along a plane generally parallel to the top surface of the housing, the flange having a generally concave bottom surface adapted to fit with a ridge located on the pneumatic module, the flange having two holes extending from a top surface of the flange to the bottom surface of the flange, the two holes adapted to accept two screws;
    wherein when the two screws are removed from the two holes, the filter assembly can be removed from the pneumatic module.

11. The assembly of claim 10 further comprising a handle located on the top of the housing, the handle adapted to be grasped by a hand.

12. The assembly of claim 11 wherein the handle is pivotable about an axis contained in a plane generally parallel to the top of the housing.

13. The assembly of claim 11 wherein the handle is adapted to be removed from the top face of the housing.

* * * * *